United States Patent [19]

Stadler et al.

[11] 3,932,246

[45] Jan. 13, 1976

[54] GAS SENSOR AND METHOD OF MANUFACTURE

[75] Inventors: Henry L. Stadler; Tseng-Ying Tien, both of Ann Arbor; Michael J. Esper, Detroit; Donald J. Romine, Southfield, all of Mich.

[73] Assignee: Ford Motor Company, Dearborn, Mich.

[22] Filed: Sept. 5, 1974

[21] Appl. No.: 503,590

Related U.S. Application Data

[60] Division of Ser. No. 393,698, Aug. 31, 1973, Pat. No. 3,886,785, which is a continuation-in-part of Ser. No. 198,515, Nov. 15, 1971, abandoned.

[52] U.S. Cl. ............... 156/89; 23/254 E; 73/19; 73/27 R; 106/39.5; 106/73.3; 264/60; 338/34
[51] Int. Cl.² .......................................... C04B 39/12
[58] Field of Search ....... 156/64, 89, 246, 264, 265, 156/285, 300, 309, 298; 264/56, 60, 61, 63, 67, 241; 73/19, 27 R, 421.5 R; 23/254 E; 324/36; 431/76; 338/34; 106/39.5, 41, 39.8, 73.3; 428/308, 325

[56] References Cited
UNITED STATES PATENTS

| | | | |
|---|---|---|---|
| 2,725,186 | 4/1973 | Lynch | 264/63 |
| 3,274,467 | 9/1966 | Graf | 106/73.3 |
| 3,423,517 | 1/1969 | Arrhenius | 156/89 |
| 3,611,243 | 10/1971 | Hardtl | 338/34 |
| 3,639,132 | 2/1972 | Egerton et al. | 106/73.3 |
| 3,676,820 | 7/1972 | Taguchi | 23/254 E |
| 3,717,487 | 2/1973 | Hurley et al. | 264/63 |
| 3,732,519 | 5/1973 | Taguchi | 338/34 |

*Primary Examiner*—William A. Powell
*Assistant Examiner*—J. J. Gallagher
*Attorney, Agent, or Firm*—Robert A. Benziger; Keith L. Zerschling

[57] ABSTRACT

A gas sensor, and its method of manufacture, particularly useful as an exhaust gas sensor for an internal combustion engine air/fuel ratio system, is disclosed. The sensor is comprised of a sintered ceramic body of transition metal oxide, such as titania, and includes a pair of spacedapart electrodes. As the partial pressure of oxygen in the gas being sensed varies in response to variations in the inlet air/fuel mixture ratio, the resistance of the ceramic material varies. The active portion of the sensor body is a substantially uniform body of porous ceramic material having a density of less than about 85% of theoretical density and a modulus of rupture in excess of 11,000 psi. The sensor is fabricated from a very pure transition metal oxide powder having a very fine and highly uniform particle size. The transitional metal oxide is selected so that the operating temperature of the resulting device is less than about 75% and preferably less than about 50% of the melting temperature of the metal oxide.

6 Claims, 4 Drawing Figures

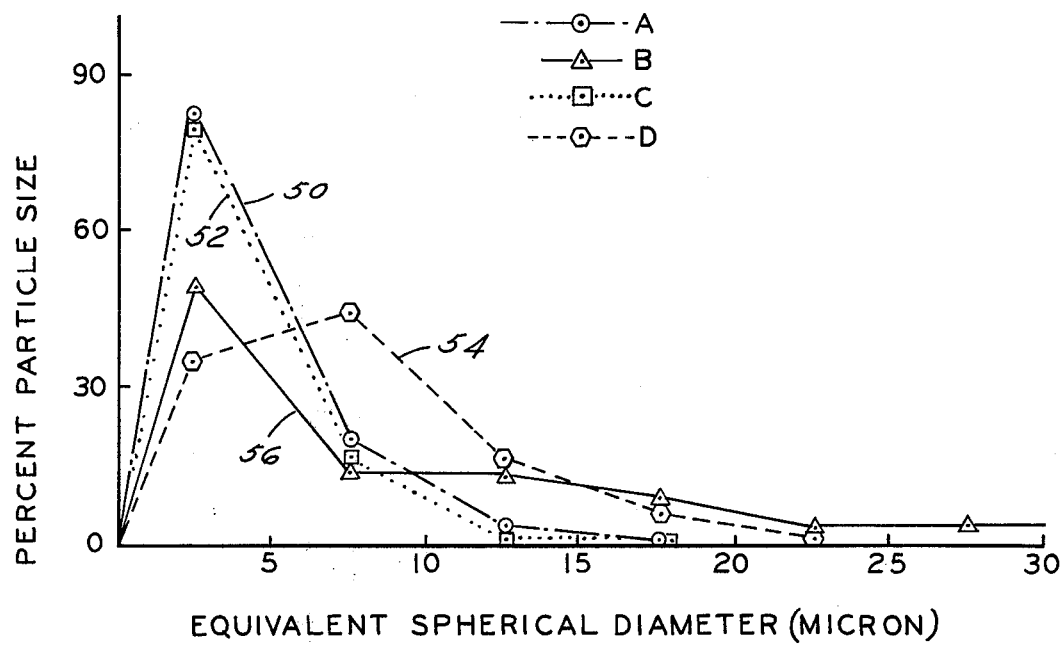

GAS SENSOR AND METHOD OF MANUFACTURE

CROSS-REFERENCE TO RELATED APPLICATIONS

This application is a division of our copending, commonly assigned U.S. patent application Ser. No. 393,698 filed Aug. 31, 1973 now U.S. Pat. No. 3,886,785 which in turn is a continuation-in-part of our Ser. No. 198,515 filed Nov. 15, 1971 now abandoned and titled "Air-Fuel Ratio Sensing System". This application is related to our co-pending, commonly assigned U.S. patent application Ser. No. 391,424 filed Aug. 23, 1973 and titled "Method of Manufacture of an Exhaust Gas Sensor for an Air-Fuel Ratio Sensing System" filed as a continuation of U.S. patent application Ser. No. 198,515.

BACKGROUND OF THE INVENTION

1. Field of the Invention

The present invention is related to the field of gas sensing devices and more particularly to that portion of the above-noted field concerned with electrical resistive devices whose resistance varies as a gas to which it is exposed varies. More particularly still, the present invention is related to that portion of the above-noted field concerned with ceramic gas sensing devices whose internal resistance varies in response to variations in the partial pressure of oxygen in the gaseous environment surrounding the device.

2. Description of the Prior Art

The temperature of the exhaust gases leaving the combustion chambers or reciprocating internal combustion engines is proportional to the amount of combustion taking place within the engine and this relationship has been used in aircraft for indicating the air-fuel ratio of the combustible mixture being supplied to the engine. Subsequent investigations showed that the thermal conductivities of various exhaust gas components could be used to indicate the proportion of such components in the exhaust gases. These investigations produced systems of the resistance bridge type that compared the thermal conductivity of the exhaust gases with known gas mixtures to indicate either air-fuel ratio or the combustion efficiency of the engine.

Recent interest in improving the environment by diminishing the quantity of undesirable components in the exhaust gases of automotive engines has accentuated investigations into systems for monitoring continuously the air-fuel ratio of combustible mixtures. These investigations have led to numerous refinements of the thermal conductivity system. For example, it was found that thermal conductivity varies almost linearly with the carbon dioxide content of the exhaust gases and carbon dioxide content in turn is proportional to the air-fuel ratio. Subsequently it was found that the thermal conductivity of the exhaust gases is a function of both the carbon dioxide content and the hydrogen content. Other approaches involved combining thermal conductivity devices with exhaust gas temperature devices.

Systems have been suggested for determining the air-fuel ratio of the mixture supplied to a combustion mechanism by detecting directly the oxidation-reduction characteristics of the exhaust gases. The system comprises a sensing member that is located in contact with either the air-fuel mixture supplied to the combustion mechanism or the exhaust gases leaving the mechanism. Two electrodes spaced apart from each other by at least a portion of the sensing member are attached to the member and to an electrical or electronic device for sensing the electrical resistance across the electrodes. The electrical resistance is proportional to the equilibrium oxygen pressure of the gaseous mixture in contact therewith and resistance measurements can be converted directly into the air-fuel ratio of the mixture supplied to the combustion mechanism.

Equilibrium oxygen pressure is the partial pressure of the oxygen in a gaseous mixture when the mixture is brought to complete chemical equilibrium. The system would thus measure equilibrium oxygen pressure of a gaseous mixture even though the gaseous mixture is not at chemical equilibrium, i.e., even though the actual pressure of the oxygen exceeds the partial pressure that would be present at equilibrium.

Sensing members for the air-fuel ratio control systems are preferably located in the exhaust gases leaving the combustion mechanism because the exhaust gases approximate more closely the desired operating temperatures of the members and do not contain any unvaporized fuel. The system is useful particularly in measuring and controlling the air-fuel ratio of the combustible mixture being supplied to an internal combustion engine.

The sensing member preferably is a relatively thin plate made from sintered particles of the desired metal compound. Useful metal compounds containing oxygen atoms and having at least two oxidation states of the metal of approximately equal energies include transition metal oxides such as titanium dioxide, vanadium oxide, chromium oxide, manganese oxide, iron oxide, nickel oxide, cobalt oxide, and rare earth metal oxides such as cerium oxide, praseodymium oxide, etc. Oxides of the metals are preferable because the ceramic properties thereof provide relatively long useful lives at higher operating temperatures and of the inherent presence of oxygen atoms. Other compounds and mixtures of the oxides with each other and with the other compounds also can be used. Energies of the two oxidation states of the metals must be sufficiently close to permit reversal by changes in the equilibrium oxygen pressure of the gases at operating temperature. Simple empirical tests may be used to determine the required relationship. The electrodes are attached to a surface of the plate or embedded with the plate. One preferred construction involves sandwiching the electrodes between two green ceramic plates and firing the assembly into a unitary structure.

Maintaining the sensing member within a relatively broad temperature range, typically about 600°–900°C., produces adequate indications of the air-fuel ratio supplied to an engine despite the fact that temperature variations change the resistance between the electrodes. Temperatures below 600°C. tend to coat the member with soot and other particulate impurities while temperatures above 900°C. tend to decrease overall life. Accuracy improvements are achieved by associating a controlled electrical heater with the sensing member to maintain its temperature within a narrower range. A highly useful structure involves a sandwich made of three green ceramic plates with the electrodes between an outer plate and the middle plate and an electrical resistance wire between the middle plate and the other outer plate. A thermocouple for temperature control can be embedded with either the electrodes or the resistance wire.

It is believed that the metal ions of the metal compounds are reduced or oxidized from one oxidation state to the other in proportion to the reducing or oxidizing nature of the exhaust gases. In the case of titanium dioxide molecules, for example, reduction frees an electron that conducts current much more readily and thereby reduces the resistance of the portion of the ceramic material located between the electrical leads.

In order for the sensing member to operate effectively in the automotive environment the sensing member must be capable of withstanding the temperature extremes and the thermal cycling normally encountered in the exhaust system and must demonstrate a response time which is at least as rapid as the response time demonstrated by the slowest engine component or by the transport properties of the fluid medium and the engine. For example, the sensor must demonstrate a response time no slower than 1 second, and preferably on the order of about 0.1 second or faster, in recognizing and responding to a change in the exhaust gas chemistry.

Ceramic materials are generally recognized as being compatible with the temperature extremes and the temperature excursions normally encountered in the engine exhaust system. In order to demonstrate the requisite service life requirement, however, the sensor response must not vary noticeably over its service life. This requires that the ceramic be chemically stable and not demonstrate substantial grain growth during its service life since this would alter its electrical properties. Furthermore, the ceramic material must demonstrate substantial strength since the automotive exhaust system environment is a mechanically harsh environment wherein substantial stressing through vibration and thermal shock and cycling may be encountered. It is therefore an object of the present invention to provide a ceramic sensor suitable for use in the exhaust system of an automotive vehicle internal combustion engine. In order to provide a suitable sensor, the ceramic used must be sufficiently porous that the exhaust gases will readily permeate the sensor, while the sensor must be sufficiently strong to withstand the exhaust environment. It is therefore a specific object of this invention to provide a partial pressure of oxygen sensor having high porosity and improved strength. More particularly, it is an object of this invention to provide a ceramic, resistive type partial pressure of oxygen sensor having high porosity and improved strength. Our above-noted co-pending applications describe a method of forming a ceramic exhaust gas sensor in the form of a substantially uniform and solid pellet of ceramic material which is capable of withstanding the automotive enviroment. The sensor theredescribed demonstrates a strong switching characteristic, that is, the resistance of the ceramic body varies over a wide range, as the air-fuel ratio of the combustion mixture varies slightly from the stoichiometric ratio. Such a sensor is of great utility when it is desired to operate the associated engine at the stoichiometric mixture ratio. However, nonstoichiometric operation of the associated engine causes the sensor to operate in a region of resistance where the changes of resistance in response to mixture ratio changes is slight and approximately linear. Sensors fabricated in accord with the broad teachings of the above-noted applications do not provide sufficiently repeatable results. It is therefore a specific objective of the present invention to provide an improved porous transition metal oxide ceramic sensor capable of reliable operation at nonstoichiometric mixture ratios. It is also an object of the present invention to provide a ceramic exhaust gas sensor which provides repeatable results, from sensor to sensor and during the life of any one sensor, when the air-fuel ratio is desired to be nonstoichiometric. It is a still further object of the present invention to provide such a sensor which has a response time of less than one second.

The exhaust gas sensor described in the above-noted patent applications has many desirable attributes. For example, with the exception of the various electrical wires and electrodes it is a porous, relatively small ceramic mass capable of being formed in various sizes and configurations. It does not require the use of any dissimilar materials such as housing, substrate, or interspersed particles. It is also fully immersed in the gas being sensed and does not require exposure to a reference. It is therefore a further object of the present invention to provide a sensor having the hereinbefore mentioned objects and having the further object of being comprised of an essentially uniform and porous ceramic body. It is also an object of the present invention to provide a method of producing such a sensor.

SUMMARY OF THE PRESENT INVENTION

We have found that suitable ceramic sensor materials require a transition metal oxide having a melting temperature which is at least 133% and preferably at least 200% of the expected operating temperature and being capable of forming a thin ceramic pellet with a modulus of rupture (MOR) in excess of 11,000 psi. Furthermore, the pellet must also have a density of from about 72 to about 84% of its theoretical density and a porosity such that the average open-pore diameter is from about 0.4 to about 0.7 of a micron with a total open pore volume of from about 0.04 to about 0.1 cubic centimeters per gram. Values outside of these ranges result in fabrication problems and/or in operational inadequacies such as short operational life or slow response time.

The ceramic sensor material having these properties is fabricated from an essentially pure and substantially uniformly sized powder any one particle of which is smaller than 20 microns at its maximum dimension. In the case of multiphase materials such as titania the powder is at least 80% comprised of the high temperature stable phase. The material is mixed with an organic binder/solvent system having high viscosity so as to result in a nonflowable slurry which is then formed into a thin sheet of material. The slurry is dried to remove the solvent thereby producing the "green ceramic". The suitable sensor shapes are formed from the green ceramic and are assembled with suitable electrical leads and wires to form a composite and the composite structure is thereafter fired into a unitary body.

BRIEF DESCRIPTION OF THE DRAWINGS

FIG. 4 is a graph illustrating powder particle size content of four ceramics tested in developing the sensor of the present invention and its new method of manufacture.

DETAILED DESCRIPTION

Figure 1:
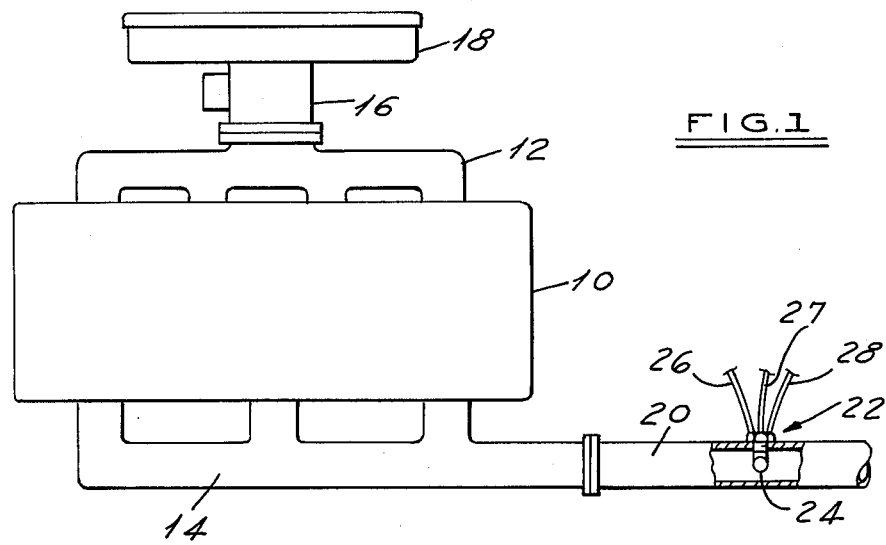
FIG. 1 is a schematic illustration of a reciprocating internal combustion engine showing the installation in the exhaust pipe of a sensing member of this invention.

Referring to FIG. 1, a reciprocating internal combustion engine 10 includes an intake manifold 12 for delivering an air-fuel mixture to the engine combustion chambers (not shown) and an exhaust manifold 14 for removing the combustion products from the combustion chambers. A carburetor 16 is attached to the intake manifold and an air cleaner 18 is attached to the air inlet of carburetor 16. Carburetor 16 receives fuel from a fuel source (not shown), produces an air-fuel mixture and supplies the air-fuel mixture to intake manifold 12.

Exhaust manifold 14 is connected to an exhaust pipe 20. Threaded into the wall of exhaust pipe 20 is a plug-shaped member 22 comprising a disc-shaped ceramic sensing member 24 according to the present invention. Three sets of electrical leads 26, 27 and 28 extend from the top of plug-shaped member 22.

Figure 3:
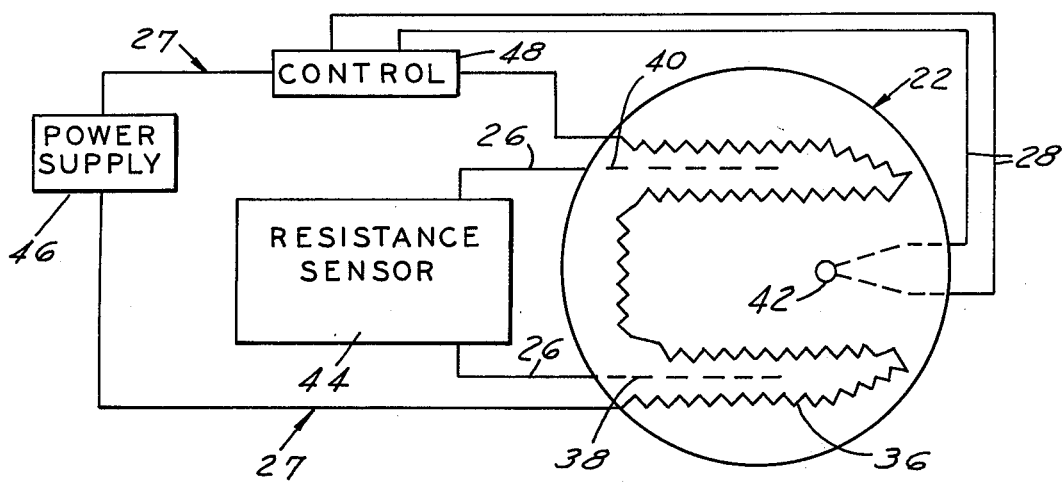
FIG. 3 is a sectional elevation of the disc-shaped sensing member of FIG. 2 showing the disposition of the electrodes, an electrical resistance heating wire, and a thermocouple in a sandwich construction.
Figure 2:
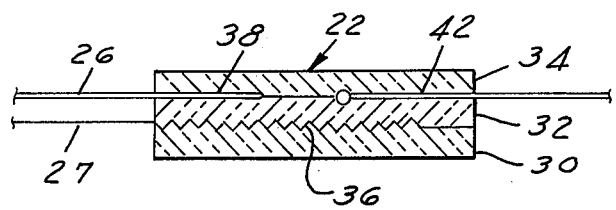
FIG. 2 is a schematic plan view of a disc-shaped sensing member of this invention showing the electrical connections thereto.

Turning to FIGS. 2 and 3, sensing member 22 comprises a sandwich of three thin ceramic plates 30, 32 and 34. A length of electrical resistance wire 36 is sandwiched between plates 30 and 32. Two electrodes 38 and 40 and a thermocouple 42 and sandwiched between plates 32 and 34. Electrodes 38 and 40 are spaced apart a considerable distance as shown in FIG. 2. The entire sandwich is fired into a unitary structure by conventional ceramic firing techniques.

Electrical leads 26 connect electrodes 38 and 40 to an electrical resistance sensor 44 as shown in FIG. 2. Leads 27 connect the ends of the resistance wire 36 to an electrical power supply 46 and leads 28 connect thermocouple 42 to a control circuit 48 located between the power supply and one end of the resistance wire.

Each of plates 30, 32 and 34 consists essentially of a transition metal oxide ceramic with the one presently preferred being titanium dioxide. Each plate has a final thickness of about 0.008 inch and a diameter of about 0.25 inch. The plates are made by a cast tape process that comprises casting a titanium dioxide slurry onto a plastic carrier tape, evaporating the vehicle from the slurry, stripping the plastic tape and punching discs from the remaining green ceramic layer. The process is given in greater detail hereinbelow.

Resistance wire 36 typically is made of platinum alloyed with about 13% rhodium and is about 0.008 inches in diameter. Electrodes 38 and 40 typically are made of platinum and are about 0.008 inches in diameter. Thermocouple 42 is a gold-palladium-platinum and gold-palladium combination. The green plates, resistance wire, electrodes and thermocouple are sandwiched together as shown and isostatically pressed. After pressing, the assembly is fired to form a unitary body.

The resulting disc is installed in the exhaust conduit of a reciprocating internal combustion engine where exhaust gases will heat the disc to about 700°C. When the engine is supplied with an air-fuel mixture of about 13:1, the resistance across the electrodes is about 5 ohms. Changing the air-fuel to 14:1 without changing any other engine parameters increases the resistance to about 10 ohms. An air-fuel ratio of 15:1 produces a resistance of 20,000 ohms. It will be appreciated that these values are intended to be illustrative and that specific values will depend on the configuration of the ceramic body as well as the electrical properties of the ceramic and the process of fabrication.

Actual values of electrical resistance depend also on the distance between the electrodes and temperature. These factors tend to shift the entire resistance vs. air-fuel ratio curve without affecting significantly the shape of the curve. Resistance changes rapidly in the vicinity of the stoichiometric air-fuel ratios and considerable temperature variations can be tolerated when measurements are being made in that vicinity. Resistance values change much more slowly at ratios away from stoichiometric and the present invention provides a sensor having much more reliable and predictable values for non-stoichiometric operation of the engine.

A wide variety of materials can be used to make the electrodes, resistance wire and thermocouple used in the sensing member. The sensing member also can be formed in a wide variety of sizes and shapes including cylinders, squares, rectangles, etc. However, care should be taken to match, as closely as possible, the coefficients of thermal expansion.

In fabricating sensors according to the present invention very pure titania powder was obtained through normal commercial channels from Cerac Pure, Inc. Such powders are normally at least about 99.5% pure titania ($TiO_2$). As titania has two phases, the anatase and the rutile and the rutile phase represents the high temperature stable phase, the anatase phase majority material was calcined and ball milled to produce powder having small particle sizes and with the majority being rutile phase material. Calcining also improves the purity of the powder by volatilizing any volatilizable impurities. Table I sets forth the processing steps in order to achieve the conversion and also sets forth the weight percentages of the rutile verses the anatase phase in each of the samples A, B, C and D. Table I also sets forth the powder sizes and distributions for each of these test samples.

TABLE I

|  | Lot A | Lot B | Lot C | Lot D |
| --- | --- | --- | --- | --- |
| Raw Material | Titania, 95% anatase | Titania, 85% rutile | Titania, 95% anatase | Titania, 95% anatase |
| Calcining Cycle | 2 hrs. at 2100°F. | None | 2 hrs. at 2100°F. | 2 hrs. at 2500°F. |
| Milling Time | 16 hrs. | None | 5 hrs. | 5 hrs. |
| Phase Composition (after calcining) |  |  |  |  |
| Wt % Rutile | 80 | 85 | 85 | 100 |
| Wt % Anatase | 20 | 15 | 15 | 0 |
| Particle Size (wt%) (see FIG. 1) |  |  |  |  |
| 44 microns | 100 | 100 | 100 | 100 |
| 20 microns | 100 | 88 | 100 | 100 |
| 10 microns | 98 | 64 | 99 | 79 |

TABLE I-continued

|  | Lot A | Lot B | Lot C | Lot D |
|---|---|---|---|---|
| 5 microns | 82 | 50 | 80 | 35 |
| 2 microns | 42 | 32 | 45 | 13 |
| 0.5 microns | 7 | 5 | 3 | 6 |

The processed powders were then ball milled with an organic binder solution to form a slurry and were thereafter formed into a tape or sheet of material. A representative composition of a ball mill organic binder system is presented in Table II. After milling, the slurry was deaired and cast to form a sheet or tape of material. In this instance a doctor blade was used to control the thickness of the tape to yield a thicnkess of approximately 15 mils when air dried.

TABLE II

| Material | Wt. % |
|---|---|
| Ceramic | 45.3 |
| Solvent | 41.0 |
| Wetting Agent | 0.2 |
| Binder | 6.2 |
| Plasticizer | 7.3 |

The sensors were fabricated by taking two pieces of the ceramic tape and coating them with a small amount of solvent to develop a tackiness on the surface. The pieces were placed together and laminated using an 8000 pound uniaxially applied load and thereafter small disc shapes were punched from the laminate with a standard paper punch. The size was merely for convenience and of course other sizes and shapes are contemplated. Platinum heater wires were fabricated by bending 8 mil wire around stationary pins to form an "M" type configuration. This configuration allows substantially uniform heating of the pellet shaped sensor. A light application of solvent was applied to the surface of one ceramic disc and a heater was lightly pressed into the surface. A second disc was placed on top of the heater and the unit was lightly pressed together to form a heater pellet. To assure uniform heating for purposes of deriving test data, two of these heater pellet assemblies were used to provide a uniform temperature across the sensor pellet although in practice a single heater mechanism as shown in FIG. 3 will be sufficient. A thermocouple and a pair of spaced apart electrodes were placed on one of the heater pellet assemblies and given a light coat of solvent. A second heater pellet assembly was placed on top of the first and the total sensor assembly was lightly pressed and allowed to dry at room temperature for approximately 30 minutes. The sensor assembly was placed in a rubber sack which was then sealed and placed in the oil chamber of an isostatic press and pressed at 1000 psi to insure good contact between the various components of the sensor assembly and between the powder particles of the ceramic.

The sensor assembly was covered with titania coated paper to protect it from contamination. It was then placed in an oven and heated at 150°F. for 12 hours. The temperature was then raised to 285°F. and a vacuum of 27 inches of mercury was pulled on the oven. The assembly was left in vacuum for 12 hours. The vacuum removes the volatile substances, that is the solvents which may cause bubbles within the sensor assembly during the sintering process. After bakeout, the organic binder and nonvolatilizable plasticizer constitute less than about 20% of the green pellet assembly.

The paper package containing the sensor was then placed in a kiln and the temperature raised to the sintering temperature for a time period sufficient to accomplish maturing, that is initial or partial sintering, by firing to a pyrometric cone equivalent number 9. The actual temperatures used were 2200° and 2300°F. for sensors from each.

The material identified by the designation D was found to produce unsatisfactory sensors due to the fact that a large amount of cracking occurred during the firing phase. It is believed that this cracking occurred because the size range and distribution of particles included within this D material was too great when considering the small thickness of the ceramic. The completed sensors using the A, B and C materials were then tested for performance by placement in an atmosphere which approximated the exhaust gas environment of an automobile. The gaseous constituents of the test atmosphere were varied and the electrical resistance changes of the sensors were measured in terms of the time lag demonstrated by the sensors in response to changes in the gaseous atmosphere. The sensors fabricated from the materials identified as A and C were found to yield acceptable performance results in terms of repeatability for any one sensor and in terms of the time response to changes in the gaseous atmosphere. However, the sensors fabricated from material B were found to change in response to changes in the gaseous environment with a time lag several multiples of the time lag experienced by the A and C sensor materials.

This time lag is believed to be the result of increased gas pentration time, that is, the time required for the gas to permeate the pores of the sensor so as to change the sensor resistance. Only open pores were considered in making these measurements. Table III gives the average pore diameter and total pore volume for sensors fabricated from the A, B, C and D materials for two firing temperatures. Since the B material devices were much slower responding, it appears that the figures given in Table III for the B material sensors represent values below the minimum values.

TABLE III

OPEN PORE VOLUME AND AVERAGE OPEN PORE SIZE OF TITANIA

| Lot | Sintering Temp. (°F) | Average Pore Diameter (microns) | Total Pore Volume (cc/gm) |
|---|---|---|---|
| A | 2200 | 0.59 | .059 |
| A | 2300 | 0.65 | .042 |
| B | 2200 | 0.35 | .036 |
| B | 2300 | 0.25 | .033 |
| C | 2200 | 0.42 | .069 |
| C | 2300 | 0.42 | .050 |
| D | 2200 | 1.90 | .178 |
| D | 2300 | 2.30 | .157 |

From the Table III figures, it appears that the minimum average pore diameter must be about 0.4 microns while minimum total pore volume must be about 0.04 cubic centimeters per gram. While decreased response time and increased sensitivity are believed to be directly controlled by porosity and sensors fabricated from the D material has the largest total open pore volume and the largest open pore diameter, the inability of these sensors to resist cracking and fracturing during firing and/or during testing renders the D material sensors of little or no practical value. Cracking and fracturing is believed to be caused by nonuniform grain growth within the ceramic. Since the high values of average open pore diameter and total open pore volume can be directly related to the grain size and grain packing, it appears that, at least for the small pellet-type sensors described hereinabove, maximum values of average open pore diameter and total open pore volume intermediate the smallest values for the D material and the largest values for the A and C material sensors are required. Values of average open pore diameter less than about 0.7 microns and of total open pore volume less than about 0.1 cubic centimeters per gram are believed to be appropriate.

Examination of the particle size distribution figures from Table I provides information to explain the differing porosities. The sensors fabricated from materials A and C had powders which were smaller than 20 microns with 75% of the powder being finer than 5 microns and at least 90% sized between 10 and 0.5 microns while the B material did not meet any of these criteria and the D material satisfied only the criteria pertaining to the largest permissible particle. It is thus apparent that generalized criteria can be expressed. Firstly, the powder particles must be very small and secondly, the particle size distribution must also be small. A wide range of sizes is exhibited by both the B and D materials and it was determined that neither was suitable.

With reference to Table IV, it can be seen that the D material sensors had the lowest density further suggesting good porosity which is varified by Table III. However, the failure to have a narrow particle size distribution made the sensors, in the small configuration consonant with good heat-up time and fast response time, impossible to fabricate. Conversely, the B material sensors were too dense to response rapidly to changes in the gas sample.

TABLE IV

| Lot | DENSITY OF TITANIA Firing Temp. (°F.) | % Theoretical |
| --- | --- | --- |
| A | 2200 | 80.2 |
| A | 2300 | 85.0 |
| B | 2200 | 86.9 |
| B | 2300 | 87.8 |
| C | 2200 | 77.6 |
| C | 2300 | 82.6 |
| D | 2200 | 57.1 |
| D | 2300 | 60.2 |

Referring now to FIG. 4, a graph illustrating the particle powder size content and distribution for sensors fabricated from the Lot A, B, C and D materials is shown. This graph is taken from the data of powder particle size content and distribution given in Table I and graphically illustrates the differences in powder particle size content of the four lots of ceramic material. The two curves identified as 50 and 52 represent the materials of Lots A and C respectively. The sensors fabricated from these materials produced the best overall results both from a performance and from a fabrication view point. These curves peak at a very high percentage value of about 75% particle size being about 5 microns equivalent spherical diameter. The curves thereafter drop off rapidly and reach a zero percentage content at a value between 15 and 20 microns equivalent spherical diameter. The Lot D material is represented by curve 54. This material demonstrated the highest porosity and also demonstrated cracking and fracturing during firing and use. This curve 54 differs markedly, having a much lower peak percentage value, in the neighborhood of 50%, at a particle size between 5 and 10 microns equivalent spherical diameter. This demonstrates that the particle size content of the Lot D material was fairly uniformly distributed over a range of particle sizes running from about 10 microns equivalent spherical diameter down to a value of about 2 microns equivalent spherical diameter. While this material would demonstrate a packing such that a large number of voids and pores could be expected, under gain growth conditions it would be expected that the larger grains formed, for example, from the ten micron particle size material or larger would grow at the expense of the smaller grains of ceramic formed from the particles having a particle size of 2 microns or less. This growth would tend to fill the pores or voids and would also tend to cause uneven internal stressing to produce the observed cracking or fracturing.

The Lot B material demonstrates a curve 56 which is somewhat similar to the curve 50, 52 in that it has a peak value in the same range of particle sizes as demonstrated by these curves but the Lot B material contained aa considerable percentage of particles whose initial size was 7 microns equivalent spherical diameter or larger and in fact contained particles larger than 30 microns equivalent spherical diameter. This material demonstrated the least amount of porosity and also demonstrated the greatest response time which rendered it unsuitable for an automotive environment. This is readily explained when one considers that any voids or pores which would be formed adjacent the large diameter particles would be readily filled by the small diameter particles which were reasonably abundant in this material. From a consideration of data of Table I and the graphical representation of this data presented in FIG. 4, one can readily see that in the order to provide a ceramic material suitable for use in the method of the present invention and in fabricating a sensor according to the present invention, the initial particle powder size must contain a very high percentage of particles situated in a very narrow range of particle sizes.

From the above data it can be seen that extremely fine powders in a narrow particle size range, formed from primarily single high temperature stable phase crystal material with controlled high purity produce a superior exhaust gas oxygen sensor. The resultant sensor has a closely controlled porosity which is achieved by avoiding the mixing of particle sizes which the conventional ceramic processing stresses. These exhaust gas oxygen sensors have a controlled pore size distribution and large total pore volume as is required to achieve rapid gas exchange rates, high sensitivity and rapid response to exhaust gas oxygen concentration changes. Concurrently, by having an MOR in excess of 1100 psi, the sensor provides adequate thermal and mechanical shock resistance and sufficient resistance to hydrothermal corrosion to allow trouble free operation in the relatively hostile automotive exhaust gas environment for a considerable period of time sufficient to allow several tens of thousands of miles of operation without requiring alteration or replacement of the sensor.

In order to achieve the high mechanical strength requirements, the particle-to-particle bond strength must be maximized while limiting the mass transfer between adjacent grains of the ceramic material. This requires a green ceramic having the maximum possible porosity when all particles are just touching one another and a well-controlled firing process. This produces what may be a conveniently viewed as a mass of essentially spherical particles each having approximately the same diameter in a closely packed environment with the points of contact between adjacent spheres being sintered to form a continuous though porous body.

We claim:

1. A method of manufacturing a porous ceramic gas sensor comprising the steps of:

forming a fine powder from a transition metal oxide, said powder being at least 99% pure;

forming a slurry of said powder and an organic binder solution, the organic binder solution being capable of drying such that the binder will comprise less than about 20%, by weight, of the dried slurry;

drying the slurry in a sheet so that the organic binder constituent is less than about 20% by weight of the dried slurry;

cutting the sheet to provide a plurality of complementarily sized green ceramic wafers;

sandwiching a pair of electrodes in spaced-apart relation between a first pair of said green ceramic wafers; and maturing the sandwiched green ceramic laminae to a density of from about 72 to about 85% of theoretical density.

2. The method of claim 1 including further sandwiching a heater means between a second pair of wafers having a wafer common to the first pair of wafers prior to the step of maturing the sandwiched green ceramic laminae.

3. The method of claim 1 wherein the step of forming a fine powder includes the step of sizing the powder to assure that 100% of the powder is less than 20 microns in size.

4. The method of claim 1 wherein the step of forming a fine powder includes the step of sizing the powder to assure that at least about 90% of the powder is sized from about 10 microns to about 0.5 microns.

5. The method of claim 1 wherein the step of forming a fine powder includes the step of milling the powder until the powder is 100% less then 20 microns, with at least about 90% of the powder being less than 10 microns and at least about 75% of the powder being less than 5 microns.

6. The method of claim 1 wherein the step of forming a fine powder includes the step of calcining the powder to provide at least 80% of the powder as a high temperature stable phase.

* * * * *